US00PP24390P3

(12) United States Plant Patent
Suphachadiwong

(10) Patent No.: US PP24,390 P3
(45) Date of Patent: Apr. 15, 2014

(54) ***PHALAENOPSIS* PLANT NAMED 'SUPHAL1202'**

(50) Latin Name: ***Phalaenopsis* hybrid**
Varietal Denomination: SUPHAL1202

(75) Inventor: Thumrong Suphachadiwong, Chonburi (TH)

(73) Assignee: Suphachatwong Innovation Co., Ltd (TH)

( * ) Notice: Subject to any disclaimer, the term of this patent is extended or adjusted under 35 U.S.C. 154(b) by 0 days.

(21) Appl. No.: 13/573,447

(22) Filed: Sep. 14, 2012

(65) Prior Publication Data

US 2014/0082795 P1 Mar. 20, 2014

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Cassandra Bright

(57) ABSTRACT

A new and distinct *Phalaenopsis* cultivar named 'SUPHAL1202' is disclosed, characterized by petals of a light purple background color and clear red-purple striping. Plants produce a significantly large number of flowers, which have a distinctive red-purple lip with a much lighter colored margin. Plants are compact. The new variety is a *Phalaenopsis*, typically produced as an indoor ornamental plant.

1 Drawing Sheet

Latin name of the genus and species: *Phalaenopsis* hybrid. Variety denomination: 'SUPHAL1202'.

BACKGROUND OF THE INVENTION

This application relates to a new cultivar of *Phalaenopsis* hybrid. The new variety is the product of a planned breeding program. The new variety originated as a seedling from the crossing of the unpatented, proprietary seed parent *Phalaenopsis* 'S6BTX' with the unpatented, proprietary pollen parent referred to as *Phalaenopsis* 'S6PFM1'. The crossing was made by the inventor in his research greenhouse in Chonburi, Thailand in May of 2002.

The new variety was first selected by the inventor, Thumrong Suphachadiwong, a citizen of Thailand, in December of 2008, in a research greenhouse belonging to the inventor in Chonburi, Thailand. After identifying the new variety as a potentially interesting selection, the inventor continued confidential testing and propagation of 'SUPHAL1202', assessing stability of the unique characteristics of this variety.

Asexual reproduction of the new cultivar 'SUPHAL1202' was first performed at a commercial laboratory in Chonburi, Thailand by tissue culture in December of 2008. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SUPHAL1202' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPHAL1202.' These characteristics in combination distinguish 'SUPHAL1202' as a new and distinct *Phalaenopsis* cultivar:

1. Significant high flower count per plant.
2. Unusual compact plant shape.
3. Petals of a light purple background color and clear red-purple striping.
4. Red-purple lip with a much lighter colored margin.

PARENT COMPARISON

Plants of the new cultivar 'SUPHAL1202' are similar to the seed parent, *Phalaenopsis* 'S6BTX' in most horticultural characteristics. The new variety, however, has a different colored flower than the seed parent.

Plants of the new cultivar 'SUPHAL1202' are similar to the pollen parent, *Phalaenopsis* 'S6PFM1' in most horticultural characteristics. Plants of the new variety, however, produce smaller flowers, with a different color pattern than the pollen parent.

COMMERCIAL COMPARISON

'SUPHAL1202' is similar in most horticultural characteristics to the unpatented commercial variety *Phalaenopsis* 'SUPHAL1103' in most horticultural characteristics. The new variety, however, produces striping on the petals of a lighter purple color than that of 'SUPHAL1103'. The new variety also produces a lip with more purple coloration than that of 'SUPHAL1103'. The dorsal sepal of the new variety is narrower than that of 'SUPHAL1103', and the callus color is a lighter shade of yellow than that of 'SUPHAL1103'.

'SUPHAL1202' is similar in most horticultural characteristics to the unpatented commercial variety *Phalaenopsis* 'Chunli' in most horticultural characteristics. The new variety, however, produces an apical lobe of a different shape and darker, more purple coloration compared to the purple-red of 'Chunli'. The new variety also produces smaller flowers and smaller, lighter green leaves than those of 'Chunli'.

BRIS6BTX DESCRIPTION OF THE PHOTOGRAPH

The accompanying photograph in FIG. 1 illustrates in full color a typical plant of 'SUPHAL1202' grown in a commercial greenhouse in Zuidbroek, the Netherlands. This plant is approximately 18 months old after delasking, shown planted in an 11 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'SUPHAL1202' plants grown in a greenhouse in Zuidbroek, the Netherlands. Temperatures ranged between 18° C. and 28° C. day and night. No photoperiodic or chemical treatments were given to the plants. During bright Summer conditions, shade was given. During dark Winter months, supplemental light was given at unspecified amounts. Measurements and numerical values represent averages of typical plant types.

Botanical classification: *Phalaenopsis* hybrid 'SUPHAL1202'.

PROPAGATION

Type of propagation typically used: Tissue culture.
Time to initiate roots: About 21 days at approximately 28° C.
Time to produce a rooted cutting/liner: About 26 weeks at approximately 18° C. to 28° C.
Root description: Thick (typical for *Phalaenopsis*) and rounded, average diameter: 5 mm, colored greyed-green; near RHS 198D.

PLANT

Growth habit: Monopodial.
Height from to of soil line to top of foliage: Average 8.5 cm.
Height from to of soil line to top of flowers: Average 32.2 cm.
Plant spread: At widest, average: 31.5 cm; at narrowest: 23.0 cm.
Normal pot size: 11 cm.
Growth rate: Moderate.
Number of leaves per plant: Average 8.

FOLIAGE

Leaf:
- *Arrangement*.—Distichous.
- *Average length*.—Approximately 10.7 cm.
- *Average width*.—Approximately 6.2 cm.
- *Shape of blade*.—Obovate.
- *Aspect*.—Horizontal.
- *Apex*.—Unequal acute.
- *Base*.—Cuneate. Sheath length: Average 1.2 cm. Sheath width: Average 1.4 cm. Sheath color: Green to yellow-green; in between near RHS 143C and 146C.
- *Margin*.—Entire.
- *Texture of top surface*.—Smooth, glossy, very slightly furrowed.
- *Texture of bottom surface*.—Smooth, glossy.
- *Color*.—Young foliage upper side: Green; near RHS N137B. Young foliage under side: Green near RHS 143C. Mature foliage upper side: Green; near RHS N137B. Mature foliage under side: Green to yellow-green; in between near RHS 143C and 144A.
- *Venation*.—Type: Camptodromous. Venation coloration: upper side green; near RHS N137B, under side green and yellow-green; RHS 143C and 144A, main vein on under side green; near RHS 143A.

Petiole: No petioles present.

FLOWERING CHARACTERISTICS

Flower bud:
- *Rate of opening*.—Fully open approximately 5 days after stage described.
- *Length*.—Approximately 1.3 cm.
- *Diameter*.—Approximately 1.2 cm wide and 1.4 cm high.
- *Shape*.—Broad ovate.
- *Color*.—Purple; near RHS 75B, striped greyed-red; near 182C and flushed yellow-green; 150D.

Peduncle:
- *Length*.—Approximately 35.6 cm.
- *Width*.—Approximately 0.35 cm.
- *Aspect*.—Approximately 60° angle to rosette.
- *Strength*.—Strong.
- *Texture*.—Smooth, not very glossy.
- *Color*.—Green; near RHS 143A.

Inflorescence:
- *Flowers per stem*.—Average 24.
- *Inflorescence arrangement*.—Panicle.
- *Inflorescence height*.—Approximately 17.4 cm. (measured from lowest branching of panicle to top of inflorescence).
- *Inflorescence width*.—Approximately 18.5 cm.

Individual flowers:
- *Flower type*.—Single zygomorphic.
- *Shape*.—Obovate.
- *Length* (*height*).—Approximately 4.7 cm.
- *Width*.—Approximately 4.0 cm.
- *Depth*.—Approximately 2.8 cm.
- *Fragrance*.—No fragrance.
- *Persistent*.—Non-persistent.
- *Petals*.—Quantity of Petals: 2. Arrangement: One petal on each side of the column. Length: Approximately 2.3 cm. Width: Approximately 2.3 cm. Shape: Deltoid. Apex: Rounded. Base: Cuneate. Margin: Entire. Texture: Upper (forward) surface: smooth, dull, moderately velvety. Texture: Lower (back) surface: smooth, dull, moderately velvety. Color: When opening, forward surface: Purple; near RHS 77D, veined red-purple; near RHS 72B, margin white, near RHS N155C. When opening, back surface: Red-purple; near RHS 69B, veined darker; near RHS 70B, margin white, near RHS N155B. Fully Opened, forward surface: Purple; in between near RHS 76C and 77D, veined red-purple; near RHS 72B, margin white, near RHS N155C. Fully Opened, back surface: Red-purple; near RHS 69D, veined darker; near RHS 70B, margin white, near RHS N155C. Fading, forward surface: Not fading, only becoming non-velvety. Fading, back surface: Not fading, only becoming non-velvety. Color Venation Fully Opened, forward surface: Red-purple; near RHS 72B. Fully Opened, back surface: Red-purple; near RHS 70B.

*Labellum*.—Shape: Three-parted. Length: Approximately 2.3 cm. Width: Approximately 1.9 cm. Texture: Smooth, dull, slightly velvety. Tip: Cleft. Base: Cuneate. Color: When opening, forward surface: Central lobe red-purple; near RHS 61A but darker, colored purple towards the margins; near RHS N78A, lateral lobes red-purple; near RHS 61A, colored red-purple to purple towards the margins and top; near 72B and N80B, outer margins of central and lateral lobes white; near RHS N155C and N155D, callosities yellow; near RHS 3B, dotted brown; near RHS 200B and 200C. When opening, back surface: Central lobe purple; near RHS N78A, lateral lobes red-purple; near RHS 61A, colored red-purple to purple towards the margins and top; near N80B, outer margins of central and lateral lobes white; near RHS N155B. Fully Opened, forward surface: Central lobe red-purple; near RHS 72A but darker, colored purple towards the margins; near RHS N78A, lateral lobes purple; near RHS N78A, colored purple-violet towards the margins and top; near N80B, outer margins of central and lateral lobes white; near RHS N155C callosities yellow; near RHS 4C, dotted brown; near RHS 200B and 200C. Fully Opened, back surface: Central and lateral lobes purple-violet; near RHS N80A, colored lighter towards the margins and top; near N80D, outer margins of central and lateral lobes white; near RHS N155B. Fading, forward surface: Not fading, only becoming non-velvety. Fading, back surface: Not fading, only becoming non-velvety. Color Venation Fully Opened, forward surface: No venation visible. Fully Opened, back surface: No venation visible. Margin: Entire.

Sepals:

*Quantity*.—3.

*Appearance*.—Smooth, dull, moderately velvety.

*Length*.—Approximately 2.4 cm.

*Width*.—Approximately 1.7 cm.

*Shape*.—Ovate.

*Apex*.—Broad bluntly acute.

*Base*.—Broad cuneate.

*Margin*.—Entire.

*Texture*.—Smooth, dull, moderately velvety.

*Color*.—Fully Opened, forward surface: Purple; in between near RHS 76C and 77D, veined red-purple; near RHS 72B, margin white, near RHS N155C. Fully Opened, back surface: Red-purple; near RHS 69B, veined darker; near RHS 70B, margin white, near RHS N155C.

Pedicels:

*Length*.—Approximately 2.7 cm.

*Diameter*.—Approximately 0.2 cm.

*Angle*.—Approximately 85° to peduncle.

*Strength*.—Moderately strong.

*Texture*.—Smooth, moderately glossy.

*Color*.—Yellow-green; near 146D, distal part purple; 75D and 76D.

REPRODUCTIVE ORGANS

*Stamens, style and stigma fused into column?*.—Yes.

*Column length*.—Approximately 1.0 cm.

*Column diameter*.—Approximately 0.5 cm.

*Column color*.—White; near RHS N155C, striped purple; near RHS 75A.

*Ovary*.—Position: Inferior. Diameter: Approximately 0.3 cm. Color: Green-white; near RHS 157D.

*Pollinia color*.—Yellow-orange; near RHS 21A.

OTHER CHARACTERISTICS

Disease resistance: Neither resistance nor susceptibility to the normal diseases found in *Phalaenopsis* has been observed.

Drought tolerance and cold tolerance: Normal for species.

Fruit/seed production: No fruits/seeds detected to date.

What is claimed is:

1. A new and distinct cultivar of *Phalaenopsis* plant named 'SUPHAL1202' as herein illustrated and described.

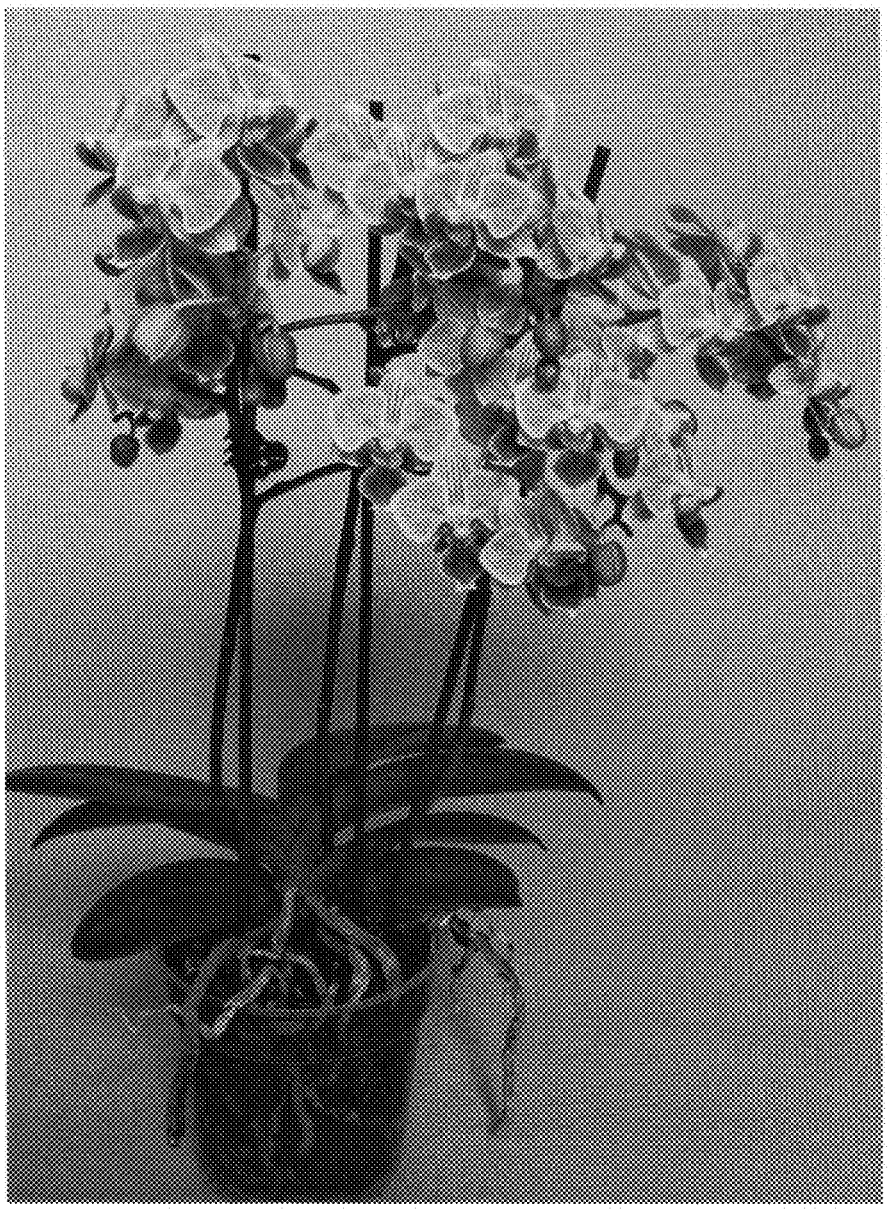

* * * * *